United States Patent [19]

Rasberger

[11] Patent Number: 4,579,682
[45] Date of Patent: Apr. 1, 1986

[54] PHOSPHONOUS ACID MONOESTER-MONOAMIDES

[75] Inventor: Michael Rasberger, Riehen, Switzerland

[73] Assignee: Ciba-Geigy Corporation, Ardsley, N.Y.

[21] Appl. No.: 558,214

[22] Filed: Dec. 5, 1983

Related U.S. Application Data

[62] Division of Ser. No. 271,319, Jun. 8, 1981, Pat. No. 4,434,109.

[30] Foreign Application Priority Data

Jun. 16, 1980 [CH] Switzerland .......................... 4617/80

[51] Int. Cl.$^4$ ................................................. C07F 9/65
[52] U.S. Cl. ................................ 260/239 B; 544/337; 546/21; 546/22; 558/157
[58] Field of Search ............................ 546/2; 544/337; 260/239 B

[56] References Cited

FOREIGN PATENT DOCUMENTS 0042359 12/1981 European Pat. Off. .............. 546/21

Primary Examiner—Alan L. Rotman
Attorney, Agent, or Firm—Luther A. R. Hall

[57] ABSTRACT

Phosphonous acid monoester-monoamides of the formula

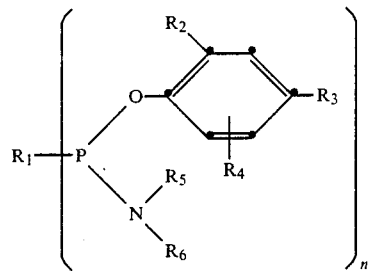

in which n is 1 or 2, when n is 1, $R_1$ is alkyl or phenyl, or when n is 2, $R_1$ is phenylene-Y-phenylene where Y is a direct bond, —O—, —S— or alkylidene, $R_2$, $R_3$ and $R_4$ are independently hydrogen or alkyl and $R_5$ and $R_6$ together with the N-atom to which they are bonded from a heterocyclic ring, are suitable for protecting organic material from the harmful effect of heat, oxygen and light.

8 Claims, No Drawings

PHOSPHONOUS ACID MONOESTER-MONOAMIDES

This is a divisional of application Ser. No. 271,319, filed on June 8, 1981, now U.S. Pat. No. 4,434,109, issued Feb. 28, 1984.

The present invention relates to novel phosphonous acid monoester-monoamides, their preparation, their use as stabilisers for organic material and the organic material stabilised with the aid of these novel compounds.

It is known that phosphonous acid derivatives can be employed as stabilisers for protecting organic material from the harmful effect of heat, oxygen and light. Thus, stabilisers for organic material which have been described are phosphonous acid diamides, in German Offenlegungsschrift No. 2,113,380, inter alia, and phosphonous acid diesters, in European Patent Application No. 5,447.

The present invention relates to phosphonous acid monoester-monoamides (called phosphonous acid ester-amides in the text which follows), which have excellent properties in respect of stabilisation during processing, storage stability, adsorption of water, sensitivity to hydrolysis, dyeing, volatility, migration, compatibility and light stabilisation improvement.

The novel compounds have the formula I

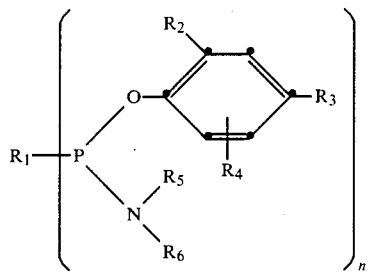

(I)

in which n is 1 or 2 and, if n is 1, $R_1$ is $C_1$–$C_{18}$ alkyl, styryl or biphenylyl, or phenyl which can be substituted by one to three $C_1$–$C_8$ alkyl groups and/or one di-($C_1$–$C_{12}$)-alkyl-amino group in the 4-position, and $R_2$ and $R_4$ independently of one another are $C_1$–$C_{18}$ alkyl, $C_5$–$C_{12}$ cycloalkyl, phenyl, benzyl, α-methylbenzyl or α,α-dimethylbenzyl, and $R_4$ can also be hydrogen, and $R_3$ is hydrogen, $C_1$–$C_{18}$ alkyl, $C_1$–$C_{18}$ alkoxy, $C_2$–$C_{19}$ alkoxycarbonyl or $C_3$–$C_{24}$ alkoxycarbonylalkyl, or $C_8$–$C_{16}$ phenoxycarbonylalkyl, or phenoxycarbonyl which is unsubstituted or substituted by one to three $C_1$–$C_8$ alkyl groups, or $R_3$ is phenyl, benzyl, α-methylbenzyl, α,α-dimethylbenzyl or one of the groups II or III

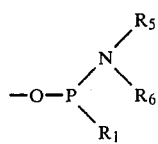

(II)

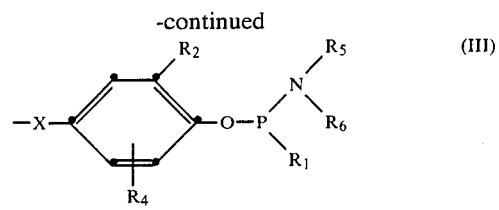

(III)

in which $R_1$, $R_2$ and $R_4$ are as defined above, $R_5$ and $R_6$ are as defined below, X is —O—, —S— or —($R_7$)C($R_8$)— and $R_7$ and $R_8$ independently of one another are hydrogen or $C_1$–$C_8$ alkyl, or $R_3$ and $R_4$ together are a 1,1,3,3-tetramethyl-1,3-trimethylene radical which is fused on in the 4-position and 5-position, and $R_5$ and $R_6$ independently of one another are $C_1$–$C_{22}$ alkyl, $C_2$–$C_{21}$ oxaalkyl, $C_2$–$C_{21}$ thiaalkyl, $C_3$–$C_{18}$ alkenyl, $C_3$–$C_{18}$ alkinyl, $C_2$–$C_6$ hydroxyalkyl, $C_3$–$C_{24}$ alkoxycarbonylalkyl, $C_5$–$C_{12}$ cycloalkyl, $C_6$–$C_{14}$ aryl, $C_7$–$C_{15}$ alkaryl or $C_7$–$C_{15}$ aralkyl, or a $C_5$–$C_{17}$ piperidin-4-yl group which is substituted or unsubstituted, and $R_5$ can also be hydrogen or a group of the formula IV

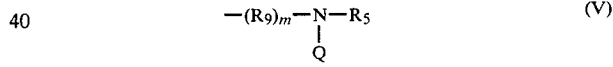

(IV)

in which $R_1$, $R_2$ and $R_4$ are as defined above and $R_3^*$ has the same definition as $R_3$, with the exception of the groups of the formulae II and III, and $R_6$ can also be one of the groups V or VI

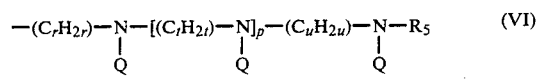

(V)

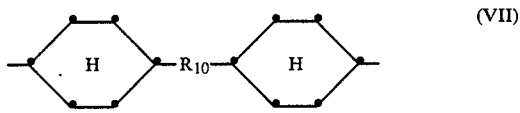

(VI)

in which Q is a group of the formula IV, in which $R_1$, $R_2$, $R_3^*$ and $R_4$ are as defined above, and m is zero or 1 and $R_9$ is alkylene which is uninterrupted or interrupted by one or two oxygen or sulfur atoms, $C_4$–$C_{22}$ alkenylene, $C_4$–$C_{22}$ alkinylene, $C_5$–$C_9$ cycloalkylene or a group of the formula VII (VII)

in which $R_{10}$ is —O—, —S— or —($R_{11}$)C($R_{12}$), in which $R_{11}$ and $R_{12}$ independently of one another are hydrogen or $C_1$–$C_8$ alkyl, or $R_{11}$ and $R_{12}$, together with the C atom to which they are bonded, are $C_5$–$C_{12}$ cycloalkyl, or $R_{11}$ and $R_{12}$ together are 1,4-cyclohexylenedimethylene or 1,3,3-trimethyl-1,5-cyclohexylene, or $R_9$ is phenylene, biphenylene or a group of the formula VIII

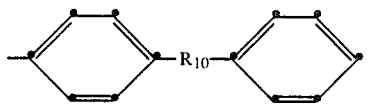
(VIII)

in which $R_{10}$ is as defined above, and r, t and u independently of one another are 2, 3, 4, 5 or 6, p is zero, 1, 2 or 3 and $R_5$ in the formulae V and VI is as defined above, or, in the formula I, $R_5$ and $R_6$, together with the N atom to which they are bonded, form a substituted or unsubstituted pyrrolidine, oxazolidine, piperidine, morpholine, piperazine or hexamethyleneimine ring or a group of the formula IX

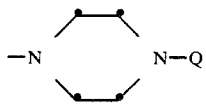
(IX)

in which Q is as defined above, and, if n is 2, $R_1$ is a group of the formula X

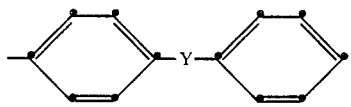
(X)

in which Y is a direct bond, 1,4-phenylene, —O—, —S— or —($R_7$)C($R_8$)—, in which $R_7$ and $R_8$ are as defined above, and $R_2$, $R_3$ and $R_4$ are as defined above, $R_5$ is as defined above but is not a group of the formula IV and $R_6$ is as defined above but is not one of the groups of the formulae V and VI.

A $C_1$–$C_{18}$ alkyl radical $R_1$, $R_2$, $R_3$ or $R_4$ is, for example, methyl, ethyl, n-propyl, iso-propyl, n-butyl, sec.-butyl, t-butyl, n-pentyl, t-amyl, n-hexyl, 2-methylpentyl, 2,4-dimethylpentyl, n-octyl, 6-methylheptyl, 2-ethylhexyl, 1,1,3,3-tetramethylbutyl or straight-chain or branched nonyl, decyl, dodecyl, tridecyl, tetradecyl, hexadecyl or octadecyl. An alkyl radical $R_2$ is preferably $C_1$–$C_8$ alkyl and, in particular, tertiary $C_4$–$C_8$ alkyl, such as t-butyl, t-amyl or 1,1,3,3-tetramethylbutyl. An alkyl radical $R_3$ is preferably $C_1$–$C_{12}$ alkyl, and in particular $C_1$–$C_8$ alkyl. An alkyl radical $R_4$ preferably has 1-8 C atoms.

A phenyl radical $R_1$ can be substituted by one to three $C_1$–$C_8$ alkyl groups, and preferably by one to three $C_1$–$C_4$ alkyl groups. Examples of these radicals are o-tolyl, m-tolyl, p-tolyl, o-xylyl, m-xylyl, p-xylyl, mesityl, o-cumyl, p-t-butylphenyl, 2,4-di-t-butylphenyl, 2,4,6-tri-t-butylphenyl and 2,4-di-(1,1,3,3-tetramethylbutyl)-phenyl. A phenyl radical $R_1$ can also be substituted in the 4-position by a di-($C_1$–$C_{12}$)-alkyl-amino group. Examples of these radicals are 4-dimethylaminophenyl, 4-diethylaminophenyl, 4-di-isopropylaminophenyl, di-n-butylaminophenyl, di-n-octylaminophenyl, di-(2-ethylhexyl)-aminophenyl and di-n-dodecylaminophenyl. Alkyl groups having 1-4 C atoms are preferred. In particularly preferred compounds, $R_1$ is $C_1$–$C_{18}$ alkyl or phenyl.

A $C_5$–$C_{12}$ or, in particular, $C_5$–$C_7$ cycloalkyl radical $R_2$, $R_4$, $R_5$ or $R_6$ can be cyclopentyl, cycloheptyl, cyclooctyl, cyclononyl, cyclododecyl or, in particular, cyclohexyl.

$R_2$ is also preferably phenyl or benzyl, and in particular α-methylbenzyl or α,α-dimethylbenzyl. In preferred compounds, $R_4$ is hydrogen or $C_1$–$C_8$ alkyl, which is preferably in the 6-position.

A $C_1$–$C_{18}$, preferably $C_1$–$C_8$, alkoxy radical $R_3$ is, for example, methoxy, ethoxy, iso-propoxy, iso-butoxy, n-butoxy, t-butoxy, n-hexyloxy or straight-chain or branched octyloxy, dodecyloxy or octadecyloxy.

A $C_2$–$C_{19}$ alkoxycarbonyl radical $R_3$ can be, for example, methoxycarbonyl, ethoxycarbonyl, iso-propoxycarbonyl, n-butoxycarbonyl or straight-chain or branched octoxycarbonyl, dodecyloxycarbonyl, tetradecyloxycarbonyl or octadecyloxycarbonyl.

A $C_3$–$C_{24}$ alkoxycarbonylalkyl radical, preferably a $C_3$–$C_{20}$ alkoxycarbonylmethyl or $C_4$–$C_{21}$ alkoxycarbonylethyl radical, $R_3$, $R_5$ or $R_6$ is, for example, methoxycarbonylmethyl, methoxycarbonylethyl, ethoxycarbonylpropyl, octyloxycarbonylbutyl, dodecyloxycarbonylethyl, octadecyloxycarbonylmethyl or octadecyloxycarbonylethyl.

A phenoxycarbonyl radical $R_3$ can be substituted by one to three $C_1$–$C_8$ alkyl groups. Examples of these radicals are o-tolyloxycarbonyl, m-tolyloxycarbonyl, p-tolyloxycarbonyl, o-xylyloxycarbonyl, p-xylyloxycarbonyl, mesityloxycarbonyl, o-cumyloxycarbonyl, p-t-butylphenoxycarbonyl, 2,4-di-t-butylphenoxycarbonyl, 2,4,6-tri-t-butylphenoxycarbonyl, 2,4-di-(1,1,3,3-tetramethylbutyl)phenoxycarbonyl or 2,4-di-isopropylphenoxycarbonyl.

A $C_8$–$C_{16}$ phenoxycarbonylalkyl radical $R_3$ is, for example, phenoxycarbonylmethyl, phenoxycarbonylethyl, pheenoxycarbonylpropyl, phenoxycarbonylhexyl, phenoxycarbonyloctyl or phenoxycarbonylnonyl. These groups can be substituted in the phenyl part by one to three $C_1$–$C_8$ alkyl groups. Examples of these radicals are o-tolyloxycarbonylmethyl, o-xylyloxycarbonylpropyl, mesityloxycarbonylethyl, 2,4,6-tri-isopropylphenoxycarbonylpropyl, 2,4-di-(1,1,3,3-tetramethylbutyloxycarbonylmethyl or 2,4-di-t-butylphenoxycarbonyloctyl.

$R_3$ is also preferably phenyl or benzyl, and in particular α-methylbenzyl or α,α-dimethylphenyl.

In a group $R_3$ of the formulae II or III, the substituents $R_1$, $R_2$, $R_4$, $R_5$ and $R_6$ are preferably as defined for the corresponding radicals in formula I.

X is —O— or —S—, and preferably a group —($R_7$)C($R_8$)—.

A $C_1$–$C_8$ alkyl radical $R_7$, $R_8$, $R_{11}$ or $R_{12}$ is, for example, methyl, ethyl, n-propyl, n-butyl, n-hexyl, n-octyl or 2-ethylhexyl. $R_7$ and $R_8$ are preferably hydrogen or methyl.

A $C_1$–$C_{22}$ alkyl radical $R_5$ or $R_6$ can be as defined above for an alkyl radical $R_1$, $R_2$, $R_3$ or $R_4$, or can be straight-chain or branched nonadecyl, eicosyl, heneicosyl or docosyl. $C_1$–$C_{18}$ alkyl groups are preferred, and $C_1$–$C_{12}$ alkyl groups are particularly preferred.

A $C_2$–$C_{21}$ oxa- or thia-alkyl radical $R_5$ or $R_6$ is, for example, methoxymethyl, methylthiamethyl, ethoxymethyl, methylthiaethyl or ethoxyethyl. Alkoxypropyl and alkylthiapropyl groups are preferred, such as methoxypropyl, ethylthiapropyl, butoxypropyl, octylthiapropyl, dodecyloxypropyl, octadecylthiapropyl and octadecyloxypropyl.

A $C_3$–$C_{18}$ alkenyl radical $R_5$ or $R_6$ is, for example, allyl, methallyl, n-hex-3-enyl, n-oct-4-enyl, n-undec-10-enyl or n-octadec-17-enyl. Allyl and methallyl are preferred, and allyl is particularly preferred.

A $C_3$–$C_{18}$ alkinyl radical $R_5$ or $R_6$ is, for example, propargyl, n-but-1-inyl, n-but-2-inyl or n-hex-1-inyl.

Alkinyl groups having 3 or 4 C atoms, in particular propargyl, are preferred.

A hydroxyalkyl radical $R_5$ or $R_6$ having 1-6 C atoms can be, for example, 2-hydroxypropyl, 2-hydroxyethyl, 3-hydroxypropyl, 4-hydroxybutyl or 6-hydroxyhexyl.

A $C_6$–$C_{14}$ aryl radical $R_5$ or $R_6$ is, for example, phenyl, α-naphthyl, β-naphthyl or phenanthryl. Phenyl groups are preferred.

An aralkyl radical $R_5$ or $R_6$ having 7-15 C atoms is, for example, benzyl, α-phenethyl, α,α-dimethylbenzyl or 2-phenethyl, preferably benzyl.

A $C_7$–$C_{15}$ alkaryl group $R_5$ or $R_6$ can be, for example, o-tolyl, m-tolyl, p-tolyl, o-xylyl, m-xylyl, p-xylyl, mesityl, 2,6-diethylphenyl, 2,4,6-triisopropylphenyl or 4-t-butylphenyl.

A $C_5$–$C_{17}$ piperidin-4-yl group $R_5$ or $R_6$ can be, for example, unsubstituted piperidin-4-yl or piperidin-4-yl which is substituted by up to 5 alkyl groups, preferably by methyl or ethyl groups. The substituents are preferably in the 2-position and 6-position of the piperidine ring. This radical can also be 3,3,5-trimethyl-8-ethoxybicyclo[4,4,0]dec-2-yl.

$R_5$ and $R_6$ can therefore form piperidin-4-yl groups of the following structure:

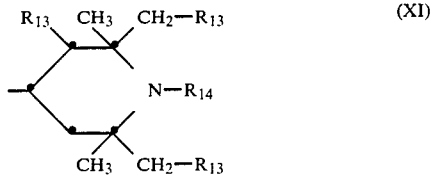

in which $R_{13}$ is hydrogen or methyl and $R_{14}$ is hydrogen, oxyl, $C_1$–$C_{18}$ alkyl, $C_3$–$C_8$ alkenyl, $C_3$–$C_6$ alkinyl, $C_7$–$C_{12}$ aralkyl, $C_2$–$C_{21}$ alkoxyalkyl, an aliphatic acyl group having 1-4 C atoms or a —$CH_2COOR_{15}$ group, in which $R_{15}$ is $C_1$–$C_{12}$ alkyl, $C_3$–$C_8$ alkenyl, phenyl, $C_7$–$C_8$ aralkyl or cyclohexyl.

Compounds of the formula I in which only one of the radicals $R_5$ and $R_6$ is a piperidin-4-yl group are preferred.

In particularly preferred compounds, only one of the radicals $R_5$ or $R_6$ is a group of the formula XI, and the other is hydrogen.

Especially preferred piperidin-4-yl radicals are those in which $R_{13}$ is hydrogen and $R_{14}$ is hydrogen, methyl or acetyl.

$R_{13}$ is particularly preferably hydrogen.

A $C_1$–$C_{18}$ alkyl radical $R_{14}$ is, for example, methyl, ethyl, n-propyl, n-butyl, n-pentyl, n-octyl, n-decyl, n-dodecyl or octadecyl. Preferred alkyl groups have 1 to 12 carbon atoms, preferably 1 to 8 carbon atoms and in particular 1 to 4 carbon atoms, and methyl is especially preferred.

A $C_3$–$C_8$ alkenyl radical $R_{14}$ is, for example, allyl, 3-methyl-2-butenyl, 2-butenyl, 2-hexenyl or 2-octenyl, in particular allyl.

A $C_3$–$C_6$ alkinyl radical $R_{14}$ is, for example, propargyl.

A $C_7$–$C_{12}$ aralkyl radical $R_{14}$ is, for example, benzyl, β-phenethyl or 4-t-butyl-benzyl, preferably benzyl.

A $C_2$–$C_{21}$ alkoxyalkyl radical $R_{14}$ can have 1 to 3 carbon atoms in the alkyl moiety and 1 to 18 carbon atoms in the alkoxy moiety, for example as in methoxymethyl, ethoxymethyl, 2-methoxyethyl, 2-ethoxyethyl, 2-n-butoxyethyl, 3-n-butoxypropyl, 2-octyloxyethyl or 2-octadecyloxyethyl; compounds in which $R_{14}$ is an alkoxyalkyl group having 2 to 6 carbon atoms are preferred.

An aliphatic acyl group $R_{14}$ having 1 to 4 carbon atoms is, for example, formyl, acetyl, acrylyl or crotonyl, in particular acetyl.

In a —$CH_2COOR_{15}$ group $R_{14}$, a $C_1$–$C_{12}$ alkyl radical $R_{15}$ is, for example, methyl, ethyl, isopropyl, n-butyl, isobutyl, t-butyl, isopentyl, n-octyl or n-dodecyl. $R_{15}$ is preferably $C_1$–$C_4$ alkyl. A $C_3$–$C_8$ alkenyl radical $R_{15}$ is, for example, allyl, 2-butenyl or 2-hexenyl. A $C_7$–$C_8$ aralkyl radical $R_{15}$ is, for example, benzyl or α-phenethyl.

In a group $R_5$ of the formula IV, the substituents $R_1$, $R_2$ and $R_4$ are preferably as defined for the corresponding radicals in formula I. $R_3$* preferably also has the same definition as $R_3$ in formula I, except that $R_3$* is not a group of the formula II or III. The same applies to a group $R_6$ of the formula V or VI, in which Q is a group of the formula IV. In preferred compounds, $R_5$ in the formula V or VI is as defined for $R_5$ in formula I.

r, t and u independently of one another are 2, 3, 4, 5 or 6. They preferably have the same value, and in particular are 2 or 3.

p is zero, 1, 2 or 3, preferably zero or 1 and in particular zero.

m can be zero or, preferably, 1.

A $C_2$–$C_{22}$ alkylene radical, preferably a $C_2$–$C_9$ and in particular a $C_2$–$C_6$ alkylene radical, $R_9$ can be, for example, dimethylene, trimethylene, tetramethylene, hexamethylene, octamethylene, nonamethylene, 2,2,4-trimethylhexamethylene, decamethylene, dodecamethylene, octadecamethylene or docosamethylene. An alkylene group which is interrupted by one or two oxygen or sulfur atoms can be 2-thia-1,3-propylene, 3-thia-1,5-pentylene, 4-oxaheptamethylene or 3,6-dioxa-1,8-octylene.

A $C_4$–$C_{22}$ alkenylene or alkinylene radical $R_9$ is, for example, 2-buten-1,4-ylene, 2-butin-1,4-ylene, 2,4-hexadiin-1,6-ylene or propen-1,3-ylene.

A $C_5$–$C_9$ cycloalkylene radical $R_9$ is, for example, 1,2-cyclopentylene, 1,2-cyclohexylene, 1,3-cyclohexylene, 1,4-cyclohexylene, 1,4-cycloheptylene or 1,2-cyclononylene. A cycloalkylene radical $R_9$ preferably has 6 C atoms.

$R_{11}$ and $R_{12}$, together with the C atom to which they are bonded, can form $C_5$–$C_{12}$ cycloalkyl. This radical is, for example, cyclopentyl, cycloheptyl, cyclooctyl, cyclononyl, cyclododecyl or, in particular, cyclohexyl.

A pyrrolidine, oxazolidine, piperidine, morpholine, hexamethyleneimine or piperazine ring formed by $R_5$ and $R_6$, together with the N atom to which they are bonded, can be substituted by one to five methyl or ethyl groups. These ring systems are preferably unsubstituted.

n can be 2 or, preferably, 1.

Preferred compounds of the formula I are those in which n is 1 or 2 and, if n is 1, $R_1$ is $C_1$–$C_{18}$ alkyl or styryl, or phenyl which can be substituted by one to three $C_1$–$C_4$ alkyl groups and/or a di-($C_1$–$C_4$)-alkylamino group in the 4-position, and $R_2$ and $R_4$ independently of one another are $C_1$–$C_8$ alkyl, $C_5$–$C_7$ cycloalkyl, phenyl, benzyl, α-methylbenzyl or α,α-dimethylbenzyl, and $R_4$ can also be hydrogen, and $R_3$ is hydrogen, $C_1$–$C_{12}$ alkyl, $C_1$–$C_8$ alkoxy, $C_2$–$C_{19}$ alkoxycarbonyl, $C_3$–$C_{20}$ alkoxycarbonylmethyl, $C_4$–$C_{21}$ alkoxycarbonylethyl, phenyl, benzyl, α-methylbenzyl or α,α-dimethylbenzyl, or one of the groups II or III, in which $R_1$, $R_2$ and $R_4$ are as defined above, $R_5$ and $R_6$ are as defined below and X is a group of the formula —$(R_7)C(R_8)$—, in which $R_7$ and $R_8$ independently of one another are hydrogen or methyl, or $R_3$ and $R_4$ together are a 1,1,3,3-tetramethyl-1,3-trimethylene radical which is fused on in the 4-position and 5-position, and $R_5$ and $R_6$ independently of one another are $C_1$–$C_{18}$-alkyl, $C_3$–$C_4$-alkenyl, $C_3$–$C_4$ alkinyl, $C_3$–$C_{20}$ alkoxycarbonylmethyl, $C_4$–$C_{21}$ alkoxycarbonylethyl, $C_5$–$C_7$ cycloalkyl, phenyl, $C_7$–$C_{15}$ alkaryl, benzyl or an optionally substituted $C_5$–$C_{17}$ piperidine-4-yl group, and $R_5$ can also be hydrogen and $R_6$ can also be a group of the formula V or VI, in which $R_5$ and m are as defined above and Q is a group of the formula IV, in which $R_1$, $R_2$ and $R_4$ are as defined above and $R_3^*$ is $R_3$, with the exception of the groups of the formulae II and III, and $R_9$ is $C_2$–$C_9$ alkylene which is uninterrupted or interrupted by one or two oxygen or sulfur atoms, cyclohexylene or a group of the formula VII, in which $R_{10}$ is —O—, —S— or —$(R_{11})C(R_{12})$—, and $R_{11}$ and $R_{12}$ independently of one another are hydrogen or methyl, or $R_{11}$ and $R_{12}$, together with the C atom to which they are bonded, are cyclohexylene, 1,4-cyclohexyldimethylene or 1,3,3-trimethyl-1,5-cyclohexylene, or $R_9$ is phenylene, and r, t and u are 2 or 3 and p is zero or 1, or $R_5$ and $R_6$, together with the N atom to which they are bonded, form a pyrrolidine, oxazolidine, piperidine, morpholine, piperazine or hexamethyleneimine ring or a group of the formula IX, in which Q is as defined above; and, if n is 2, $R_1$ is biphenylene, $R_2$, $R_3$, $R_4$ and $R_5$ are as defined above and $R_6$ is as defined above but is not one of the groups of the formulae V and VI.

Particularly preferred compounds of the formula I are those in which n is 1 or 2, and, if n is 1, $R_1$ is $C_1$–$C_{18}$ alkyl or phenyl, $R_2$ is $C_4$–$C_8$ alkyl, α-methylbenzyl or α,α-dimethylbenzyl, $R_4$ is hydrogen or $C_1$–$C_8$ alkyl, $R_3$ is hydrogen, $C_1$–$C_8$ alkyl, $C_3$–$C_{20}$ alkoxycarbonylmethyl, $C_4$–$C_{21}$ alkoxycarbonylethyl, α-methylbenzyl or α,α-dimethylbenzyl, $R_5$ and $R_6$ independently of one another are $C_1$–$C_{12}$ alkyl, allyl, cyclohexyl or a 2,2,6,6-tetramethylpiperidin-4-yl group, and $R_5$ can also be hydrogen, or $R_5$ and $R_6$, together with the N atom to which they are bonded, are piperidine, hexamethyleneimine or morpholine or a group of the formula IX, in which Q is a group of the formula IV, in which $R_1$, $R_2$ and $R_4$ are as defined above and $R_3^*$ has the same definition as $R_3$ above, and, if n is 2, $R_1$ is biphenylene and $R_2$, $R_3$, $R_4$, $R_5$ and $R_6$ are as defined above.

Compounds of the formula I in which $R_2$ is $C_4$–$C_8$ alkyl and $R_3$ and $R_4$ are hydrogen or $C_1$–$C_8$ alkyl are of particular interest.

Examples of compounds of the formula I are:

1. 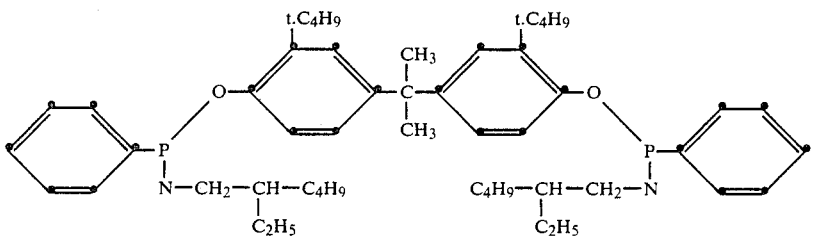

2. Phenylphosphonous acid mono-[2,6-di-t-butyl-4-(2',4'-di-t-butylphenoxycarbonyl)-phenyl]-ester monopiperidide.

3. o-Tolylphosphonous acid mono-(2,6-di-t-butyl-4-octadecyloxycarbonylethylphenyl)-ester mono-(di-n-butyl)-amide.

4. 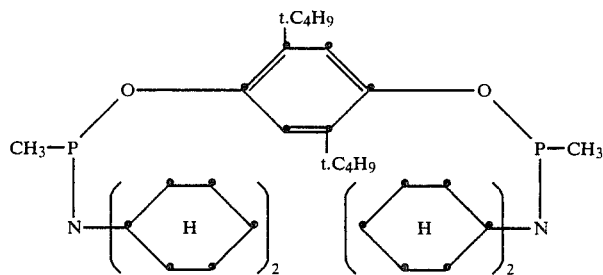

5. 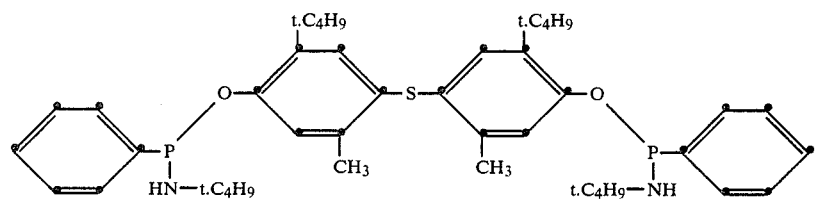

6. 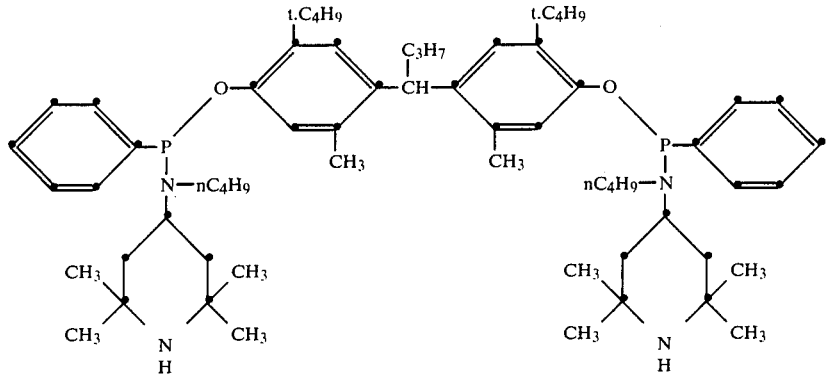
7. 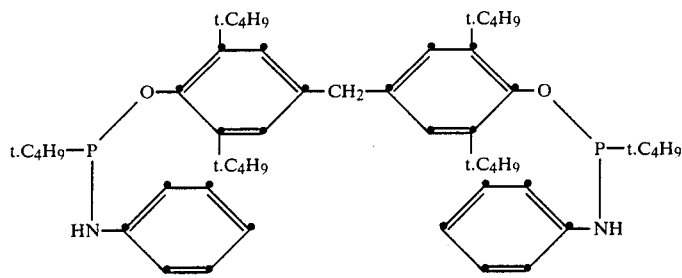
8. $Z_1$—NH—$(CH_2)_2$—N($Z_1$)—$(CH_2)_2$—NH—$Z_1$
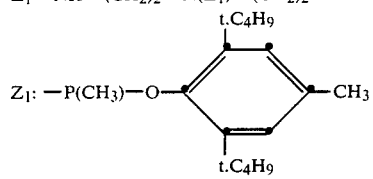
9. 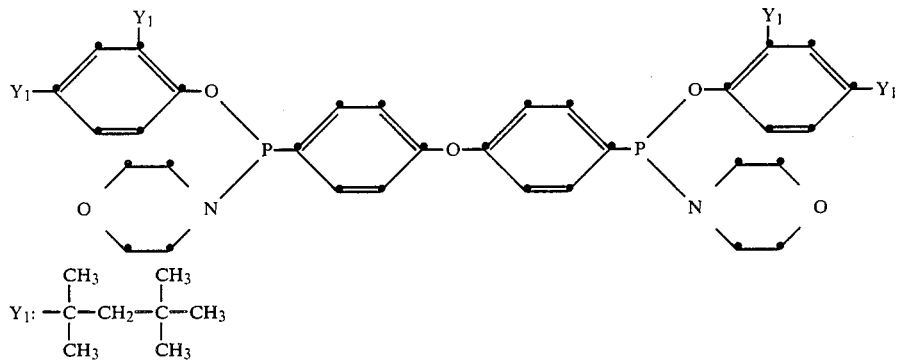
10. 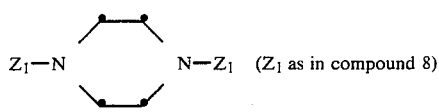 ($Z_1$ as in compound 8)
11. Phenylphosphonous acid mono-2,4-di-t-amyphenylester mono-(diallyl)-amide.
12. 4-Diethylaminopheenyl-phosphonous acid mono-(2,6-di-t-butylphenyl)-ester mono-phenylamide.
13. $(Z_2)_2$N—$C_8H_{17}$
$Z_2$: 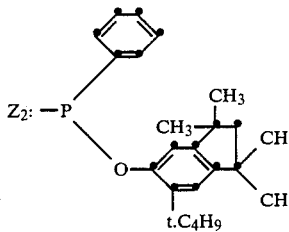

14. 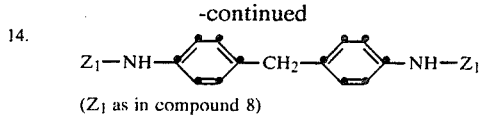

(Z₁ as in compound 8)

15. 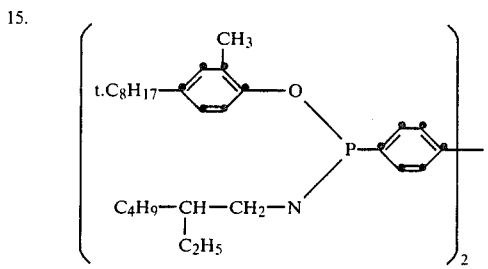

16. Phenylphosphonous acid mono-(1,1,3,3-tetramethylindan-5-yl)-ester mono-(di-cyclohexyl)-amide.

17. 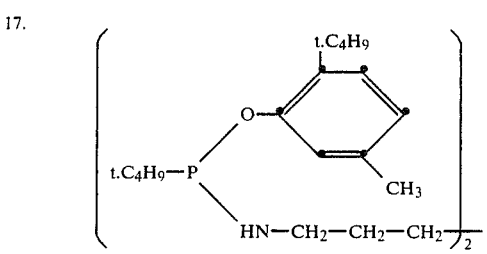

The preparation of the compounds of the formula I is known per se and can be effected, for example, by means of the amidation and esterification reactions known to the expert.

As a rule, the compounds of the formula I are prepared by reaction a compound of the formula XII

 (XII)

in which $R_1$ is as defined above and A is a reactive group, with a phenol of the formula XIII

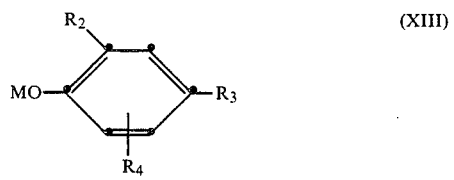 (XIII)

in which $R_2$, $R_3$ and $R_4$ are as defined above and M is hydrogen or an alkali metal, such as Na or K, and an amine of the formula XIV

 (XIV)

in which M, $R_5$ and $R_6$ are as defined above.

A reactive group A is, for example, halogen, in particular Cl, phenoxy or a —$OR_{16}$ or —$N(R_{16})_2$ group, in which $R_{16}$ is $C_1$–$C_4$ alkyl, such as methyl, ethyl, n-propyl, iso-propyl, n-butyl, sec.-butyl or t-butyl.

In this process, the compound of the formula XII can first be reacted with the phenol of the formula XIII in approximately molar amounts and the resulting intermediate of the formula XV

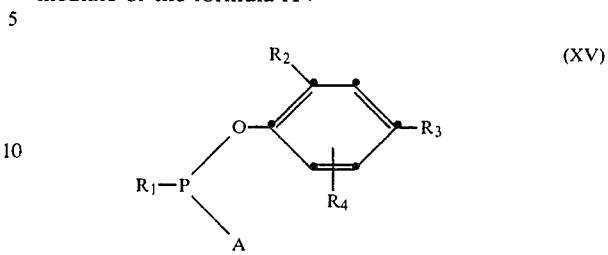 (XV)

can then be reacted with the amine of the formula XIV, the amine advantageously being employed in excess.

The two reaction steps described above can also be carried out in reverse sequence, or they can be carried out simultaneously.

The reaction can be carried out in an aprotic solvent, such as benzene, toluene, xylene, chlorobenzene, dichlorobenzene or special boiling-point spirit, at temperatures of 80°–160° C., preferably at the reflux temperature, or without a solvent at a temperature of 80°–220° C. The reaction is preferably carried out in the presence of an acid acceptor, such as $Na_2CO_3$, $NaHCO_3$, $K_2CO_3$, $KHCO_3$, NaOH, KOH or a tertiary amine, such as triethylamine or pyridine. Amine of the formula XIV employed in excess can also function as the solvent and/or as an acid acceptor.

The starting substances of the formulae XII, XIII and XIV are known compounds, or, if they are novel, they can be prepared by processes analogous to known processes.

According to the present invention, the compounds of the formula I can be used as stabilisers for organic material to protect these from damage by the action of oxygen, light and heat. Organic material which can be stabilised includes, for example:

1. Polymers of monoolefins and diolefins, for example polyethylene (which can be non-crosslinked or crosslinked), polypropylene, polyisobutylene, poly-but-1-ene, polymethylpent-1-ene, polyisoprene or polybutadiene, and polymers of cycloolefins, for example of cyclopentene or norbornene.

2. Mixtures of the polymers mentioned under 1), for example mixtures of polypropylene and polyethylene or polyisobutylene.

3. Copolymers of monoolefins and diolefins with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkylacrylate copolymers, ethylene/alkyl methacrylate copolymers, ethylene/vinyl acetate copolymers or ethylene/acrylic acid copolymers and salts thereof (ionomers), and terpolymers of ethylene with propylene and a diene, such as hexadiene, dicyclopentadiene or ethylidenenorbornene.

4. Polystyrene.

5. Copolymers of styrene or α-methylstyrene and dienes or acrylic derivatives, for example styrene/butadiene copolymers, styrene/acrylonitrile copolymers, styrene/alkyl methacrylate copolymers or styrene/acrylonitrile/methyl acrylate copolymers; high impact strength mixtures of styrene copolymers and another polymer, for example a polyacrylate, a diene polymer or an ethylene/propylene/diene terpolymer; and block copolymers of styrene, for example styrene/butadiene/styrene copolymers, styrene/isoprene/styrene copolymers, styrene/ethylene-butylene/styrene copolymers or styrene/ethylene-propylene/styrene copolymers, as well as copolymers of styrene, butadiene and acrylic acid.

6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 5), for example the mixtures known as so-called ABS, MBS, ASA or AES polymers.

7. Halogen-containing polymers, for example polychloroprene, chlorinated rubber, chlorinated or chlorosulfonated polyethylene or, in particular, polymers of halogen-containing vinyl compounds, for example polyvinyl chloride, polyvinylidene chloride, polyvinyl fluoride or polyvinylidene fluoride; and copolymers thereof, such as vinyl chloride/vinylidene chloride copolymers, vinyl chloride/vinyl acetate copolymers or vinylidene chloride/vinyl acetate copolymers.

8. Polymers which are derived from $\alpha,\beta$-unsaturated acids and derivatives thereof, such as polyacrylates and polymethacrylates, polyacrylamides and polyacrylontriles.

9. Copolymers of the monomers mentioned under 8) with one another or with other unsaturated monomers, for example acrylontrile/butadiene copolymers, acrylontrile/alkyl acrylate copolymers, acrylonitrile/vinyl chloride copolymers or acrylontrile/alkyl methacrylate/butadiene terpolymers.

10. Polymers which are derived from unsaturated alcohols and amines or their acyl derivatives or acetals, such as polyvinyl alcohol, polyvinyl acetate, stearate, benzoate or maleate, polyvinyl butyral, polyallyl phthalate or polyallylmelamine.

11. Homopolymers and copolymers of cyclic ethers, such as polyalkylene glycols, polyethylene oxide or polypropylene oxide, or copolymers thereof with bisglycidyl ethers.

12. Polyacetals, such as polyoxymethylene, and those polyoxymethylenes which contain comonomers, for example ethylene oxide.

13. Polyphenylene oxides and sulfides.

14. Polyurethanes which are derived from polyethers, polyesters and polybutadienes with terminal hydroxyl groups on the one hand and aliphatic or aromatic polyisocyanates on the other hand, and precursors thereof.

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene-terephthalamide and poly-m-phenylene-isophthalamide, and copolymers thereof with polyethers, for example with polyethylene glycol, polypropylene glycol or polytetramethylene glycol.

16. Polyureas, polyimides and polyamide-imides.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate or polyhydroxybenzoates, and block polyethers/esters which are derived from polyethers with hydroxyl end groups.

18. Polycarbonates.

19. Polysulfones and polyether-sulfones.

20. Crosslinked polymers which are derived from aldehydes on the one hand and phenols, urea or melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols as well as vinyl compounds as crosslinking agents, and also low-burning halogen-containing modifications thereof.

23. Crosslinkable acrylic resins which are derived from substituted acrylates, for example from epoxy acrylates, urethane-acrylates or polyester-acrylates.

24. Alkyd resins, polyester resins and acrylate resins which are crosslinked with melamine resins, urea resins, polyisocyanates or epoxide resins.

25. Crosslinked epoxide resins which are derived from polyepoxides, for example from bis-glycidyl ethers or from cycloaliphatic diepoxides.

26. Natural polymers, such as cellulose, natural rubber and gelatine, and polymer-homologous chemically modified derivatives thereof, such as cellulose acetates, propionates and butyrates, or the cellulose ethers, such as methylcellulose.

27. Natural and synthetic organic substances which are pure monomeric compounds or mixtures thereof, for example mineral oils, animal and vegetable fats, oils and waxes, or oils, waxes and fats based on synthetic esters (for example phthalates, adipates, phosphates or trimellitates), and mixtures of synthetic esters and mineral oils in any weight ratio, for example the mixtures such as are used as plasticisers for plastics or as spinning preparations, and aqueous emulsions thereof.

28. Aqueous emulsions of natural or synthetic rubbers, for example natural rubber latex, or latices of carboxylated styrene/butadiene copolymers.

The present invention also relates to a process for stabilising polymers against thermo-oxidative degradation during their preparation, isolation, processing and use, which comprises adding at least one compound of the formula I to the polymer.

The compounds of the formula I are incorporated in the substrate in a concentration of 0.005 to 5% by weight, calculated relative to the material to be stabilised.

0.01 to 1.0, particularly preferably 0.02 to 0.5, % by weight of the compounds, calculated relative to the material to be stabilised, are preferably incorporated into this material. Incorporation can be effected, for example, by mixing at least one of the compounds of the formula I and, where appropriate, further additives into the material by the methods customary in the art, before or during shaping, or by applying the dissolved or dispersed compounds to the polymer, if necessary with subsequent evaporation of the solvent.

The novel compounds can also be added in the form of a master batch, which, for example, contains these compounds in a concentration of 2.5 to 25% by weight, to the plastics to be stabilised.

In the case of crosslinked polyethylene, the compounds are added before crosslinking.

Accordingly, the invention also relates to plastics which have been stabilised by the addition of 0.01 to 5% by weight of a compound of the formula I and which, where appropriate, can also contain other additives. The plastics stabilised in this manner can be used in various forms, for example as films, fibres, narrow tapes or profiles, or as binders for lacquers, adhesives or putty.

Examples of further additives which can be used together with the stabilisers are: antioxidants, UV absorbers and light stabilisers, such as 2-(2'-hydroxyphenyl)-benzotriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids and acrylates, and also nickel compounds, sterically hindered amines, oxalic acid diamides, metal deactivators, phosphites, compounds which destroy peroxide, polyamide stabilisers, basic co-stabilisers, nucleating agents or other additives, for example plasticisers, lubricants, emulsifiers, fillers, carbon black, asbestos, kaolin, talc, glass fibres, pigments, fluorescent brighteners, flameproofing agents and antistatic agents.

Suitable co-stabilisers are, for example, the compounds mentioned specifically in German Offenlegungsschrift No. 2,512,895.

The invention is illustrated in more detail by the examples which follow:

EXAMPLE 1

Phenylphosphonous acid mono-(2,4,6-tri-t-butylphenyl)-ester mono-piperidide 52.4 g (0.2 mol) of 2,4,6-tri-t-butylphenol are introduced into 200 ml of triethylamine. 29.2 ml (0.2 mol) of phenyldichlorophosphine are added dropwise at room temperature in the course of 2 hours and the reaction mixture is then refluxed for 8 hours. After adding 19.7 ml (0.2 mol) of piperidine, the mixture is kept under reflux for a further 10 hours, the triethylamine is evaporated off in vacuo, the residue is taken up in toluene, the toluene mixture is filtered and the solvent is distilled off from the filtrate to give the product with a melting point of 97°–98° C.

EXAMPLE 2

Phenylphosphonous acid mono-[4-(1,1,3,3-tetramethylbutyl)-2-methylphenyl]-ester mono-(dicyclohexyl)-amide A mixture of 71.6 ml (0.3 mol) of dicyclohexylamine and 30.3 ml of triethylamine is added dropwise, at room temperature in the course of 1½ hours, to 40.3 ml (0.3 mol) of phenyldichlorophosphine dissolved in 200 ml of toluene. The mixture is then refluxed for 15 hours and a mixture of 66 g (0.3 mol) of 2-methyl-4-(1,1,3,3-tetramethylbutyl)-phenol and 30.3 ml of triethylamine is subsequently added dropwise at room temperature. The mixture is again refluxed for 15 hours, the solution is then filtered and the filtrate is evaporated in a rotary evaporator to give the product with a melting point of 84°–86° C.

EXAMPLES 3–17

The compounds which follow were prepared/analogously to Examples 1 and 2:

| Example No. | Compound | Melting point |
|---|---|---|
| 3. | Phenylphosphonous acid mono-(2,6-di-t-butylphenyl)-ester mono-piperidide | 115° C. |
| 4. | Phenylphosphonous acid mono-(2,6-di-t-butyl-4-methylphenyl)-ester mono-(di-butyl)-amide  boiling point: 170° C. (1.33 Pa) | liquid |
| 5. | 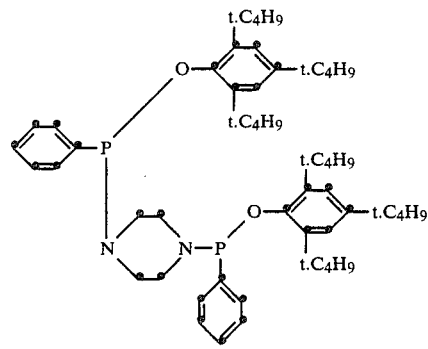 | 200–210° C. |
| 6. | Phenylphosphonous acid mono-(2,4,6-tri-t-butylphenyl)-ester mono-(di-butyl)-amide | 84° C. |
| 7. | Phenylphosphonous acid mono-(2,4,6-tri-t-butylphenyl)-ester mono-(2,2,6,6-tetramethylpiperidin-4-yl)-amide | 150° C. |

-continued

| Example No. | Compound | Melting point |
|---|---|---|
| 8. | [structure: bisphenol-A linked to two P-phenyl groups each with N(cyclohexyl)₂] | resinous |

Elementary analysis:
C_calc. 76.3%; H_calc. 8.54%; N_calc. 3.5%; P_calc. 7.7%
C_found 77.2%; H_found 9.0%; N_found 3%; P_found 7.5%

| 9. | Phenylphosphonous acid mono-(p-1,1,3,3-tetramethylbutyl-phenyl)-ester mono-(dicyclohexyl)-amide | 144° C. |
| 10. | Phenylphosphonous acid mono-[2,4-di-(1,1,3,3-tetramethylbutyl)-phenyl]-ester mono-(dicyclohexyl)-amide | 135–138° C. |
| 11. | Phenylphosphonous acid mono-(2-methyl-4-t-butylphenyl)-ester mono-(dicyclohexyl)-amide | 80° C. |
| 12. | [structure: nC₄H₉—N—P with O-phenyl(t.C₄H₉)(t.C₄H₉) and cyclohexyl, ×2] | resinous |

Elementary analysis:
C_calc. 75.72%; H_calc. 8.8%; N_calc. 2.01%; P_calc. 8.8%
C_found 75.5%; H_found 8.8%; N_found 1.7%; P_found 8.1%

| 13. | Phenylphosphonous acid mono-(2,6-di-t-butyl-4-methylphenyl)-ester mono-piperidide | 80° C. |
| 14. | Phenylphosphonous acid mono-(2,4-di-t-butylphenyl)-ester monopiperidide boiling point: 190° C. (0.133 Pa) | liquid |
| 15. | Phenylphosphonous acid mono-[p-(1,1,3,3-tetramethylbutyl)-phenyl]-ester mono-(di-isopropyl)-amide boiling point: 180° C. (0.133 Pa) | liquid |
| 16. | Phenylphosphonous acid mono-(2,4-di-t-butylphenyl)-ester mono-(di-n-butyl)-amide Boiling point 185–190° C. (0.133 Pa) | liquid |
| 17. | Phenylphosphonous acid mono-(2,4-di-t-butylphenyl)-ester mono-(dicyclohexyl)-amide Boiling point 200° C. (1.064 Pa) | liquid |
| 18. | Phenylphosphonous acid mono-(2,6-di-t-butyl-4-methyl-phenyl)-ester mono-hexamethyleneimide | 104° C. |

EXAMPLE 19

100 parts of high density polyethylene which has a molecular weight of about 500,000 ("Lupolen 5260 Z ®" in pulverulent form from BASF) and which contains 0.05 part of pentaerythritol tetrakis-[3-(3,5-di-t-butyl-4-hydroxyphenyl)]-propionate are mixed, in the dry state, with the phosphonites given in Table 1 which follows. The mixtures are kneaded in a Brabender plastograph at 220° and 50 rpm.

During this period, the resistance to kneading is continuously recorded as the torque. As a result of cross-linking of the polymer, after initially remaining constant, the torque increases rapidly in the course of kneading. The effectiveness of the stabilisers manifests itself in a prolongation of the period over which the torque remains constant.

TABLE 1

| Parts of phosphonite according to Example No. | | Time in minutes until the torque changes |
|---|---|---|
| none | | 2 |
| 0.1 part | 1 | 15 |
| 0.05 part | 1 | 12 |
| 0.1 part | 2 | 20.5 |
| 0.05 part | 2 | 11.5 |
| 0.1 part | 3 | 18.5 |
| 0.05 part | 3 | 13 |
| 0.1 part | 8 | 16.5 |
| 0.1 part | 9 | 24 |
| 0.05 part | 9 | 14.5 |
| 0.1 part | 11 | 18.5 |
| 0.05 part | 11 | 11.5 |
| 0.1 part | 13 | 15.5 |
| 0.05 part | 18 | 12 |

TABLE 1-continued

| Parts of phosphonite according to Example No. | Time in minutes until the torque changes | |
|---|---|---|
| 0.1 part | 18 | 15 |

EXAMPLE 20

100 parts of polypropylene powder (Propathene HF 20 ® from ICI) are mixed with 0.1 part of calcium stearate, the amounts of compound 11 stated in the tables which follow and pentaerythritol tetrakis-[3-(3,5-di-t-butyl-4-hydroxyphenyl)]-propionate (0.1 part in Table A).

These mixtures are extruded 5 times successively in a single screw extruder at a maximum of 260° C. on the one hand, and 3 times successively in the same extruder at 280° C. on the other hand, in each case at 100 revolutions per minute. After the 1st, 3rd and 5th extrusion on the one hand and after the 1st and 3rd extrusion on the other hand, the melt index of the polymer is measued, the load being 2,160 g, the temperature being 230° C. and the units being g/10 minutes. Degradation of the polymer manifests itself in an increase in the melt index.

TABLE A

| Parts of phosphonite according to Example No. | Melt index after several extrusions | | | | |
|---|---|---|---|---|---|
| | at 260° C. | | | at 280° C. | |
| | 1st | 3rd | 5th | 1st | 3rd |
| none | 6.3 | 8.9 | 15.0 | 7.1 | 21.4 |
| with 0.025 part of 11 | 3.2 | 4.2 | 6.1 | 4.2 | 7.6 |
| with 0.05 part of 11 | 3.1 | 3.6 | 4.3 | 3.5 | 5.2 |

What is claimed is:

1. A compound of formula I

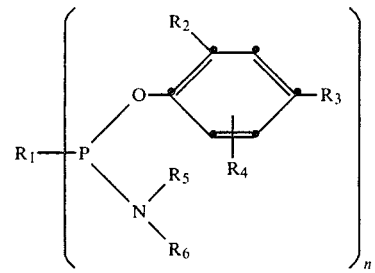

in which n is 1, $R_1$ is phenyl, $R_2$ is hydrogen or $C_1$-$C_8$ alkyl, $R_3$ is hydrogen or $C_1$-$C_8$ alkyl, $R_4$ is hydrogen or $C_1$-$C_8$ alkyl, and $R_5$ and $R_6$ together with the nitrogen atom to which they are attached represent a piperidine or hexamethyleneimine ring.

2. A compound according to claim 1 in which $R_2$ is $C_4$-$C_8$ alkyl, and $R_3$ and $R_4$ are hydrogen or $C_1$-$C_8$ alkyl.

3. The compound according to claim 1 which is phenylphosphonous acid mono-(2,4,6-tri-tert-butylphenyl)-ester monopiperidide.

4. The compound according to claim 1 which is phenylphosphonous acid mono-(2,6-di-tert-butylphenyl)-ester monopiperidide.

5. The compound according to claim 1 which is phenylphosphonous acid mono-(2,6-di-tert-butyl-4-methylphenyl)-ester monopiperidide.

6. The compound according to claim 1 which is phenylphosphonous acid mono-(2,4-di-tert-butylphenyl)-ester monopiperidide.

7. The compound according to claim 1 which is phenylphosphonous acid mono-(2,6-di-tert-butyl-4-methylphenyl)-ester monohexamethyleneimide.

8. The compound which is

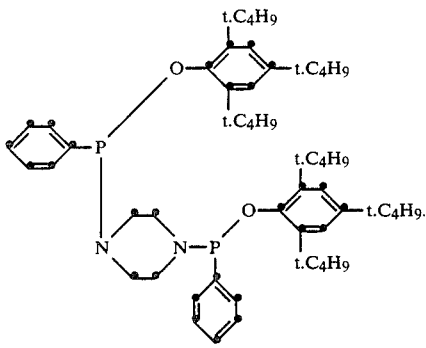

* * * * *